United States Patent [19]
Pien

[11] Patent Number: 5,327,911
[45] Date of Patent: Jul. 12, 1994

[54] UNIVERSAL CONTRACEPTIVE AND PROPHYLACTIC DEVICE

[76] Inventor: Pao C. Pien, 1105 Marbelle Club, 840 S. Collier Blvd., Marco Island, Fla. 33937

[21] Appl. No.: 42,536

[22] Filed: Apr. 5, 1993

[51] Int. Cl.$^5$ ............................................. A61F 6/04
[52] U.S. Cl. ................................. 128/844; 128/918
[58] Field of Search ................... 128/842, 844, 918; 604/330, 347–353

[56] References Cited

U.S. PATENT DOCUMENTS

| | | |
|---|---|---|
| 2,577,345 | 12/1951 | McEwen .............................. 128/844 |
| 2,591,783 | 4/1952 | Craddock . |
| 3,076,458 | 2/1963 | Mason . |
| 3,526,227 | 9/1970 | Appelbaum . |
| 3,964,485 | 6/1976 | Neumeier . |
| 4,664,104 | 5/1987 | Jaicks . |
| 4,794,920 | 1/1989 | Robichaud . |
| 4,805,604 | 2/1989 | Spery . |
| 4,834,113 | 5/1989 | Reddy . |
| 4,840,188 | 6/1989 | Heidenfelder ...................... 128/844 |
| 4,862,901 | 9/1989 | Green . |
| 4,875,491 | 10/1989 | Parrone . |
| 4,942,885 | 7/1990 | Davis et al. . |
| 4,945,923 | 8/1990 | Evans et al. . |
| 4,972,849 | 11/1990 | Park .................................... 128/844 |
| 4,981,147 | 1/1991 | Barnett . |
| 4,993,433 | 2/1991 | Reddy . |
| 4,997,427 | 3/1991 | Bowen . |
| 5,053,027 | 10/1991 | Manfredi . |
| 5,113,873 | 5/1992 | Boarman ............................. 128/844 |
| 5,136,449 | 11/1992 | van der Valk ...................... 128/844 |
| 5,156,165 | 10/1992 | Wu ....................................... 128/844 |
| 5,201,327 | 4/1993 | Johnson ............................... 128/844 |
| 5,209,242 | 5/1993 | Shields ................................. 128/844 |

FOREIGN PATENT DOCUMENTS

0429144A1 5/1991 European Pat. Off. .
WO89/01323 2/1989 World Int. Prop. O. .

*Primary Examiner*—Michael A. Brown
*Attorney, Agent, or Firm*—Roy W. Butrum

[57] ABSTRACT

A universal contraceptive and prophylactic device, and method of using the device, having a condom support device of annular configuration and including an inwardly opening groove formed on the periphery thereof, a securing device that secures the support device in place on person's body, the condom includes an elongate tubular sheath formed of thin, flexible fluid impermeable material, the condom has a closed end an open end and is sized to fit loosely about an erect male organ.

7 Claims, 1 Drawing Sheet

UNIVERSAL CONTRACEPTIVE AND PROPHYLACTIC DEVICE

BACKGROUND OF THE INVENTION

Various types of contraceptive and prophylactic devices have been developed in the prior art for the purpose of preventing the exchange of body fluids between partners during sexual intercourse. Because of the AIDS epidemic, the use of such devices to provide so-called "safe sex" has become of supreme importance to the public, and many efforts have been made to provide improved forms of protection.

Male condoms are the most common form of device to prevent conception as well as the sexual transmission of disease. However, many men are reluctant to use male condoms because of reduced sexual sensation. Female condoms have also been developed so that women can protect themselves and ensure that they are not at risk during sexual intercourse. In addition, universal contraceptive and prophylactic devices have been designed for use either by a male or female. Even though male and female condoms are readily available at the present time, the spread of the HIV virus has not been significantly slowed by the use of such condoms due to the fact that they have not proved to be satisfactory to the general public because of certain shortcomings thereof. A drastically improved device is now required which will be readily accepted by the public in order to make efforts at arresting the spread of the HIV virus successful.

Since the practice of "safe sex" is literally a matter of life and death for everyone, people should not depend on their sex partner to take necessary precautions, but rather should have the ability to personally ensure that they are properly protected. It is accordingly highly desirable to provide a universal device which can be used by either men or women and which will be sufficiently attractive to use so that there will be no objection to its use by either sex partner.

The present invention is designed to enhance rather than to diminish sexual gratification, and therefore should receive quick acceptance by the general public. The use of the invention device thereby provides the only cost effective means to effectively stop the spread of HIV virus at the present time.

SUMMARY OF THE INVENTION

The present invention is a universal contraceptive and prophylactic device which can be used by either a man or a woman with equal facility. A condom support means is provided to which a condom means is secured. The condom support means includes means for securing the support means in place on a person's body in the form of holes formed in the support means and straps extending through the holes, the straps being suitably connected to a person's body.

The condom means comprises an elongate tubular sheath formed of thin, flexible fluid impermeable material, the condom means having a closed end and an open end. The open end of the condom means includes a rim which is disposed within a groove formed in a central opening in the condom support means. The closed end of the condom means includes a portion of inwardly tapered configuration which forms a reservoir at the closed end of the condom means.

The condom means includes a main portion of a given diameter which is sized to fit loosely about an erect penis, and the condom means has a reduced diameter at the open end adjacent the rim thereof. The condom support means is annular in configuration and has an outside diameter large enough to cover the vagina opening and an inside diameter large enough to allow an erect penis to slide therethrough.

Plug means formed of soft, elastic material capable of absorbing body fluid is disposed within the sheath at the closed end thereof. This plug means is a body of revolution having a central hole formed therethrough. The plug means has a tapered configuration complementary to the tapered closed end of the sheath so as to fit snugly within the tapered closed end.

When the invention is used as a female condom, the sheath is inserted into the vagina and the plug means exerts pressure against the vagina wall to retain the closed end of the sheath in place, the open end of the sheath being secured to the condom support means which is secured in place on the woman. The plug means also serves to absorb or sponge up the body fluid from an ejaculation and thus prevents it from leaking out of the sheath, thereby providing a unique means for preventing the spread of body fluid from the man to the woman.

When the invention is used as a male condom, the condom support means and the sheath are fitted loosely over the erect penis and the condom support means is secured to the man's body in a suitable manner.

In addition, the plug means may be removed from the condom means for use either by a man or a woman under certain circumstances as will be explained hereinafter.

DESCRIPTION OF THE PREFERRED EMBODIMENT

Figure 1:
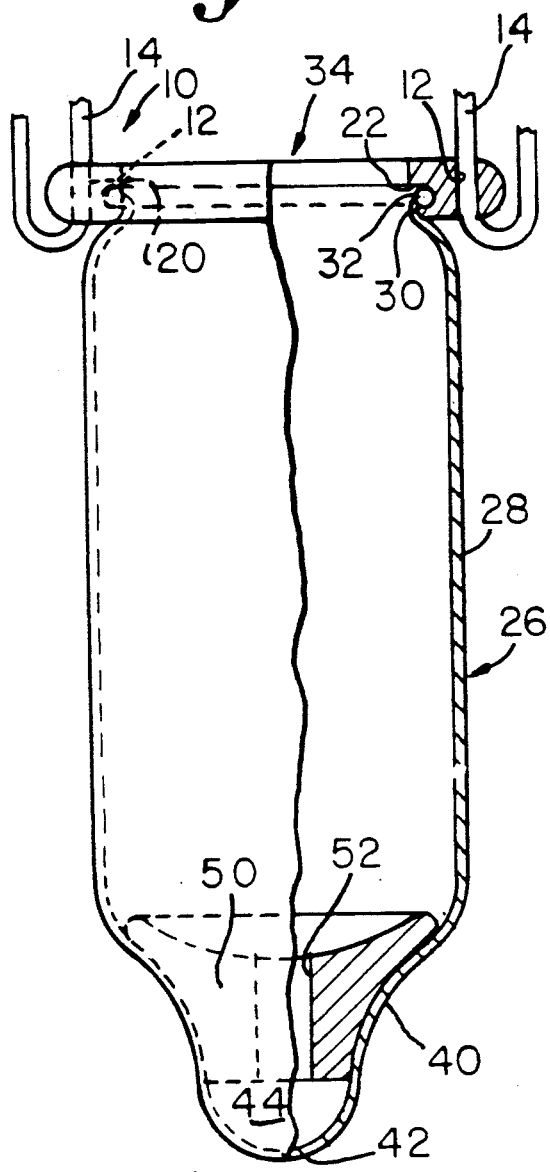
FIG. 1 is a longitudinal section through the invention device.
Figure 2:
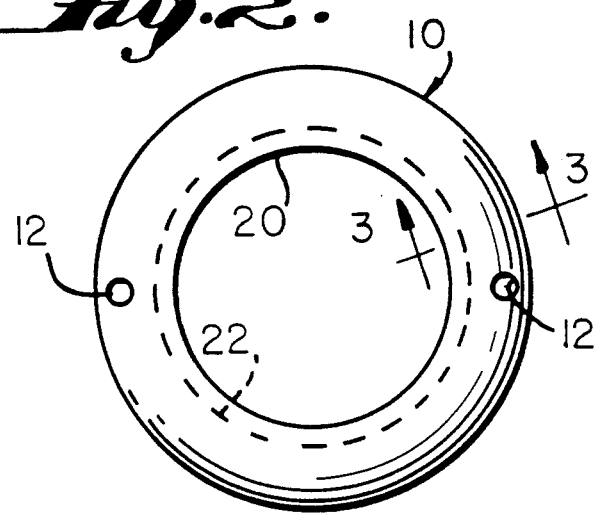
FIG. 2 is a top view of the device shown in FIG. 1.
Figure 3:
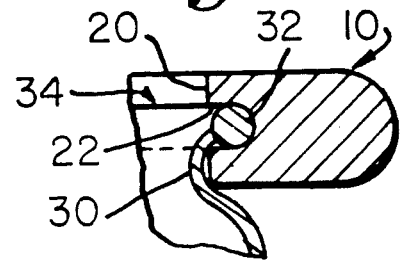
FIG. 3 is an enlarged section taken along line 3—3 of FIG. 2.

Referring now to the drawings wherein like reference characters designate corresponding parts throughout the several views, the invention incorporating the plug means is shown in FIGS. 1-3. A condom support means is indicated generally by reference numeral 10 and comprises an annular member formed of a soft yet durable substance such as soft rubber. A pair of diametrically opposite holes 12 are formed through member 10 for receiving straps 14 shown broken away in FIG. 1 for securing the condom support means in position on a person's body. These straps may be of a suitable material such as NYLON which is flexible and strong and which provides a pleasant feeling to the skin. The opposite ends of the straps may be provided with conventional attachment means such as VELCRO for connecting the straps around the thighs, or if desired, the ends of the straps may be taped to the skin. In any event, the means for securing the straps in place should be capable of being attached and detached relative to one another with little effort and with a minimum of discomfort to the skin.

Member 10 has a hole 20 formed therein which has a diameter slightly greater than an erect penis which can slide freely therethrough. An inwardly facing groove 22 is formed in the wall defining the hole and is adapted to receive the rim at the open end of an associated condom means to support the condom means.

The condom means is indicated generally by reference numeral 26 comprises an elongate tubular sheath formed of thin, flexible fluid impermeable material such as latex. The condom means includes a main portion 28 having an inner diameter adapted to fit loosely about a male penis. The main portion joins with a reduced diameter portion 30 adjacent a relatively rigid rim 32 provided at the open end 34 of the condom means. The rim is pressed into groove 22 of member 10 for supporting the condom means. This arrangement preferably enables the condom means to be detached from member 10 so that a new condom means may be attached to member 10 after the previous condom means has been used and discarded. However, the condom means may be permanently secured to member 10 if the cost of discarding member 10 after each use is acceptable.

Main portion 28 of the condom means includes a tapered portion 40 which terminates in the closed end 42 of the condom means. A reservoir 44 is provided at the closed end for receiving ejaculate. A plug means 50 shown partly in section is disposed within the condom means and is formed of soft elastic material which is capable of absorbing body fluid. The plug means may for example be formed of the same material as that used to form artificial sponges or a similar suitable material. The plug means is a body of revolution having a central hole 52 extending therethrough which provides a passage through which ejaculate may pass into reservoir 44.

It will be noted that the external surface of the plug means has a tapered configuration complementary to the tapered portion 40 of the condom means and fits snugly therewithin and in engagement therewith. The plug means may be removed from within the condom means when so desired as hereinafter described.

When the device shown in FIGS. 1-3 is used as a male condom, sheath 26 and member 10 slide loosely onto the erect penis, and member 10 is secured to the man's body by straps 14. When the penis is inserted into the vagina, the plug means presses the sheath against the vagina wall to keep the closed end of the sheath in place inside the vagina. The sheath exerts a pressure on the vagina wall to create friction between the sheath and the wall which is slightly greater than the friction between the sheath and the penis so that the inner closed end of the sheath remains stationary until the condom means is pulled outwardly by straps 14.

It is not only unavoidable, but actually desirable that there is some slack in the straps securing member 10 to the man's body. When there is such slack, plug means 50 at the closed end of the sheath does not move outward with the penis until the slack is taken up. This delay of plug means motion creates a gap between the plug means and the tip of the penis as well as between the member 10 and the base of the penis. In the following inward stroke of the penis, the sheath remains stationary until the gap between the plug means and the tip of the penis is closed. The sheath then moves inwardly with the penis and acts like a male condom. During the beginning of either an inward or an outward stroke of the penis, the sheath will not move and acts like a female condom until the plug means is pushed inwardly by the thrust of the penis or pulled outwardly by the straps.

Accordingly, the invention device functions as a female condom and a male condom on successive strokes of the penis. The proportions of the duration of these two functions can be adjusted by varying the amount of slack in the straps.

The invention device when used as a male condom also has additional advantages. The sheath of the device is loosely fitted around an erect penis without any unpleasant tight feeling such as hat caused by the use of a conventional male condom which is tightly rolled onto an erect penis and relies on the tight fit to hold it in place and prevent the escape of body fluids from the condom.

The device can assist a man in delaying his orgasm so as to achieve a simultaneous climax with his partner. At first, the device can be secured to the man's body with a minimum amount of slack in the straps. The plug means shields the sensitive penis tip to reduce the sexual sensation for delaying orgasm. Then, at a later opportune moment, the device may be released from the man's body and pushed by the penis into the vagina to become a female condom which excites the man and woman together to obtain a simultaneous climax.

When the invention device is used as a female condom, the closed end of the sheath is pushed into the vagina by pushing the plug means with a finger, and the plug means is then pushed all the way in by an erect penis. The plug means presses the sheath against the vagina wall to keep the closed end of the sheath in place inside the vagina. The condom support means is then secured to the woman's body by the straps.

The invention device has certain advantages over existing female condoms. It can be inserted into the vagina by a finger and then by an erect penis whereas prior art female condoms must be inserted with a large applicator. Furthermore, the invention device may be worn as comfortably and inconspicuously as a tampon and can be put in place beforehand whenever desired. It is far more convenient to use than existing female condoms.

The plug means of the invention is more reliable in keeping the inner end of the condom means in place than a loosely placed inner ring as used in existing female condoms so that it can be put in place and comfortably worn for long periods of time. The plug means also absorbs body fluids from ejaculation and prevents it from leaking out of the condom means, whereas body fluids can leak from prior female condoms.

The open end of the condom means is secured to the condom support means which is in turn secured to the woman's body. This is a significant improvement over a female condom wherein the outer open end dangles freely outside the vagina and can interfere with the woman's normal movements, thus preventing the condom means from being inserted in place beforehand.

Additionally, the annular condom support means formed of soft rubber or the like is so dimensioned that when a man's body presses against the annular member, it is squeezed outwardly so that it may gently touch the clitoris to provide a pleasant sensation to the woman.

Figure 4:
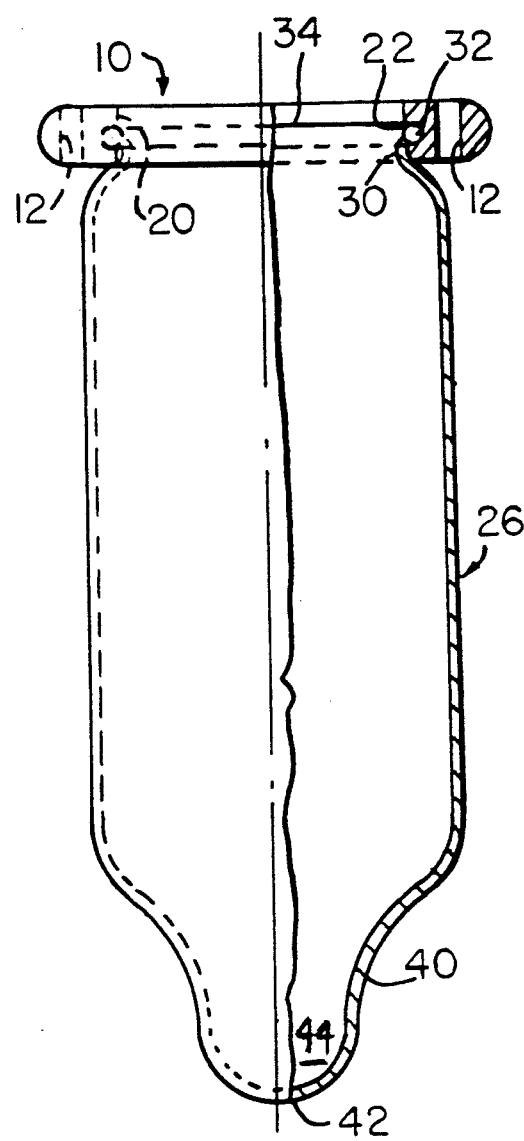
FIG. 4 is a view similar to FIG. 1 with the plug means removed.

The plug means may also be manually removed so that the device can be used as shown in FIG. 4. When the device shown in FIG. 4 is used as a female condom, there is a desirable rubbing action between the sheath and the vagina wall instead of between the sheath and the penis alone. Hence, both partners can share the sexual sensations. When the device shown in FIG. 4 is used as a male condom, the rubbing, sliding motion is also distributed between the inside and outside surfaces of the sheath. Since the plug means can be easily squeezed into or pulled out of the closed end of the sheath, the invention can be readily converted from the configuration shown in FIG. 1 to that shown in FIG. 4.

Because of the unique concept and construction of the invention, the thickness of the tubular sheath has very little influence on the sexual sensitivity and can be increased to obtain greater safety so that the failure rate can be drastically reduced. The sheath of the present invention should cost only slightly more than that of a conventional male condom since the dimensions of the invention sheath are only slightly greater.

The invention has been described with reference to a preferred embodiment. Obviously, various modifications, alterations and other embodiments will occur to others upon reading and understanding this specification. It is our intention to include all such modifications, alterations and alternate embodiments insofar as they come within the scope of the appended claims or the equivalent thereof.

What is claimed is:

1. A universal contraceptive and prophylactic device comprising condom support means of annular configuration and including an inwardly opening groove formed on the inner periphery thereof, means for securing said support means in place on a person's body, condom means comprising an elongate tubular sheath formed of thin, flexible fluid impermeable material, said condom means having a closed end and an open end and being sized to fit loosely about an erect male organ, the open end of said condom means including a rim disposed within said groove for supporting the condom means on said support means, said condom means including a main portion of a given diameter, said condom means having a reduced diameter at said open end adjacent said rim to form a shoulder and neck configuration.

2. A device as defined in claim 1 wherein the closed end of the condom means includes a portion of inwardly tapered configuration which forms a reservoir at the closed end of the condom means.

3. A universal contraceptive and prophylactic device comprising condom support means of annular configuration having an outer diameter of a size to cover a vagina opening and an inside diameter of a size to permit an erect penis to slide therethrough, said condom support means having an inwardly opening groove formed on the inner periphery thereof, said condom support means having a plurality of holes formed therethrough, strap means extending through said holes for securing the condom support means in position on a person's body, condom means comprising an elongate tubular sheath formed of thin, flexible fluid impermeable material, said condom means having a closed end and an open end and being sized to fit loosely about an erect penis, the open end of said condom means including a rim disposed within said groove for supporting the condom means on said support means, the closed end of the condom means including a portion of inwardly tapered configuration which forms a reservoir at the closed end of the condom means, said tubular sheath including a main portion of a given diameter which is sized to fit loosely about an erect penis and including a reduced diameter at said open end adjacent said rim to form a shoulder and neck configuration, and plug means formed of soft elastic material capable of absorbing body fluid and comprising a body of revolution having a central hole formed therethrough, said plug means being disposed within and in contact with the inwardly tapered portion of the condom means, said plug means having a tapered configuration complementary to the inwardly tapered portion so as to fit snugly within the inwardly tapered portion and terminating short of the outer rend of the reservoir so as to provide an open space within the reservoir beyond the plug means for receiving ejaculate.

4. A device as defined in claim 3 wherein said condom means is detachably connected to said support means.

5. The method of using a universal contraceptive and prophylactic device including condom support means of annular configuration and including an inwardly opening groove formed on the inner periphery thereof connected to securing strap means for securing the device on a person's body, the support means supporting a condom means thereon, the condom means being formed of a thin flexible fluid impermeable material defining an elongate tubular sheath having an open end and a closed end and including plug means within said closed end, comprising the steps of pushing the closed end of the sheath partially into a vagina by pushing the plug means with a finger, securing the device to a woman's body with the strap means, and pushing the sheath all the way into the vagina by an erect penis.

6. The method of using a universal contraceptive and prophylactic device including condom support means of annular configuration and including an inwardly opening groove formed on the inner periphery thereof connected to securing strap means for securing the device on a person's body, the support means supporting a condom means thereon, the condom means being formed of a thin flexible fluid impermeable material defining an elongate tubular sheath having an open end and a closed end and including plug means within said closed end, comprising the steps of securing the device to a man's body with the strap means leaving a desired amount of slack in the strap means so that in the outward stroke of a penis, the plug means does not move outward with the penis until the slack in the strap means is taken up to create a gap between the plug means and the tip of the penis, and in the following inward stroke of the penis, the sheath remains stationary until the gap between the plug means and the tip of the penis is closed whereupon the sheath moves inwardly with the penis such that during the beginning of either an outward or inward stroke of the penis, the sheath will not move and acts like a female condom until the plug means is pulled outwardly by the strap means or is pushed inwardly by the thrust of the penis.

7. The method of using a universal contraceptive and prophylactic device including condom support means of annular configuration and including an inwardly opening groove formed on the inner periphery thereof connected to securing strap means for securing the device on a person's body, the support means supporting a condom means thereon, the condom means being formed of a thin flexible fluid impermeable material defining an elongate tubular sheath having an open end and a closed end and including plug means within said closed end, comprising the steps of securing the device to a man's body with the strap means so as to have a minimum amount of slack in the strap means, commencing intercourse, and at a later opportune moment releasing the strap means from the man's body, and pushing the sheath into the woman's vagina to become a female condom, thereby exciting the man and woman together.

* * * * *